(12) United States Patent
Finnigan et al.

(10) Patent No.: US 7,635,492 B2
(45) Date of Patent: Dec. 22, 2009

(54) EDIBLE FUNGI

(75) Inventors: Timothy John Andrew Finnigan, Hutton Rudby (GB); Robin Blanchard, Stokesley (GB)

(73) Assignee: Marlow Foods Limited, Cleveland (GB)

( * ) Notice: Subject to any disclaimer, the term of this patent is extended or adjusted under 35 U.S.C. 154(b) by 463 days.

(21) Appl. No.: 10/476,751

(22) PCT Filed: Apr. 7, 2002

(86) PCT No.: PCT/GB02/02118

§ 371 (c)(1),
(2), (4) Date: Apr. 29, 2004

(87) PCT Pub. No.: WO02/090527

PCT Pub. Date: Nov. 14, 2002

(65) Prior Publication Data

US 2004/0185162 A1    Sep. 23, 2004

(30) Foreign Application Priority Data

May 4, 2001    (GB) ................ 0110954.5

(51) Int. Cl.
| A01N 65/00 | (2009.01) |
| A23G 9/00 | (2006.01) |
| A61K 39/00 | (2006.01) |
| A61K 36/06 | (2006.01) |
| A61K 36/09 | (2006.01) |

(52) U.S. Cl. .................. 424/725; 426/101; 424/157.1; 424/195.15

(58) Field of Classification Search .................. None
See application file for complete search history.

(56) References Cited

U.S. PATENT DOCUMENTS

| 2,396,592 | A | | 3/1946 | Moller | |
| 2,450,055 | A | | 9/1948 | Nord | |
| 3,993,558 | A | * | 11/1976 | Prochazka et al. | .......... 210/670 |
| 4,212,947 | A | * | 7/1980 | Torev | ...................... 435/256.8 |
| 4,293,575 | A | | 10/1981 | Cockram et al. | |
| 4,501,765 | A | * | 2/1985 | Towersey et al. | ............. 426/656 |
| 4,506,044 | A | * | 3/1985 | Cox et al. | ...................... 524/27 |
| 5,641,761 | A | | 6/1997 | Itami et al. | |
| 5,673,612 | A | | 10/1997 | Svendsen | |
| 5,738,887 | A | * | 4/1998 | Wu | ............................. 426/51 |
| 5,888,803 | A | * | 3/1999 | Starkey | .................... 435/254.1 |
| 5,904,943 | A | | 5/1999 | Finnigan et al. | |
| 5,922,374 | A | * | 7/1999 | Daury et al. | ................... 426/51 |
| 5,942,500 | A | | 8/1999 | Perry | |
| 6,010,725 | A | * | 1/2000 | Meister et al. | ................. 426/61 |
| 6,090,615 | A | * | 7/2000 | Nagaoka | ...................... 435/267 |
| 6,146,869 | A | * | 11/2000 | Harris et al. | ................. 435/198 |
| 2004/0185162 | A1 | * | 9/2004 | Finnigan et al. | ............. 426/615 |
| 2004/0197461 | A1 | | 10/2004 | Finnigan et al. | |

FOREIGN PATENT DOCUMENTS

| DE | 2848699 | | 5/1980 |
| EP | 6821 A | * | 1/1980 |
| EP | 0 761 105 A | | 3/1997 |
| EP | 0986960 | | 3/2000 |
| EP | 1190627 | | 3/2002 |
| EP | 1205114 | | 5/2002 |
| GB | 1556297 | | 11/1979 |
| JP | 60023391 | * | 2/1985 |
| JP | 08 149964 A | | 6/1996 |
| WO | WO 95 23843 A | | 9/1995 |
| WO | WO 96 21362 A | | 7/1996 |
| WO | 97/36996 | | 10/1997 |
| WO | WO 00 15045 A | | 3/2000 |
| WO | 01/67886 | | 9/2001 |
| WO | 02/089604 | | 11/2002 |

OTHER PUBLICATIONS

Murali et al., Biosynthesis of oil by *Fusarium* spp., Lebensimittel-Wissenschaft and Technologie, (1987) vol. 20, No. 6, 296-200.*
Scottawat Benjakul et al: "Effect of Chitin and Chitosan on Gelling Properties of Surimi from Barred Garfish (*Hemiramphus far*)." Journal of the Science of Food and Agriculture 81 (1) 102-108 2001 Dep. of Food Tech., Fac. of Agro-Ind., Prince of Songkla Univ., Hat Yai, Songkhla 90110, Thailand. E-Mail BSOOTTAW(A)RATREE.PSU. AC.TH, XPOO2205673, p. 102, col. 1, paragraph 2-p. 103, col. 1, paragarph 3, figure 1.
Muzzarelli, R.A. et al., "Chitin and chitinases," Birkhauser Verlag, Basel, Switzerland (1999) XP001097734, pp. 295-298, 301-310.
United States Office Action for U.S. Appl. No. 10/476,835 dated Oct. 6, 2006 (6 pages).
United States Office Action for U.S. Appl. No. 10/476,835 dated Feb. 21, 2007 (8 pages).
United States Office Action for U.S. Appl. No. 10/476,835 dated Aug. 28, 2007 (7 pages).
United States Office Action for U.S. Appl. No. 10/476,835 dated Apr. 24, 2008 (9 pages).

* cited by examiner

*Primary Examiner*—Michele Flood
*Assistant Examiner*—Qiuwen Mi
(74) *Attorney, Agent, or Firm*—Michael Best & Friedrich LLP (57) ABSTRACT

An aqueous formulation comprising edible fungal particles especially consisting substantially of fungal mycelia is described. The ingredient maybe combined with other ingredients to produce a wide range of foodstuffs or food ingredients including desserts (e.g. yogurt), reconstitutable drinks or soup and extruded foodstuffs (e.g. savory snack foods). Foodstuffs prepared may have medical applications (e.g. for treatment of joint mobility disorders, reducing fat uptake, lowering cholesterol, immune function stimulation, use on a prebiotic and/or for affecting satiety).

15 Claims, 1 Drawing Sheet

EDIBLE FUNGI

This invention relates to edible fungi and provides a method of preparing edible fungi for use in foodstuffs, formulations of edible fungi, dry particles comprising edible fungi, uses and methods associated with the aforesaid, foodstuffs per se and foodstuffs, methods and uses of edible fungi in the promotion of good health.

It is known, for example from WO 00/15045 (DSM), WO96/21362 (Zeneca) and WO95/23843 (Zeneca) to use edible filamentous fungi as meat-substitutes, for example in the preparation of burgers and sausages. In such uses, filaments of the fungi are bound together, for example with egg albumin, and are texturised so that the product resembles muscle fibres and therefore has a meat-like appearance and texture. Meat substitutes of the type described have been widely commercially available for many years under the trade mark QUORN.

The present invention, in one aspect, is based on the discovery that edible fungi can be arranged to act as fat mimetics (in sharp contrast with known uses where they are arranged to be meat-like and mimic muscle fibres) and be used in a range of foodstuffs with excellent consumer acceptability.

It is also well-known to deliver active ingredients (e.g. vitamins, minerals, pharmaceuticals etc) in tablet (or other dosage) forms. Active ingredients may be prepared synthetically, then isolated and tableted. Alternatively, active ingredients may be extracted from raw materials containing them and then tableted. It is also known to fortify foods with active ingredients (e.g. vitamins). However, in the aforesaid cases, a concentrate of substantially pure active ingredient is incorporated into the food, at low concentration and so as to have negligible effect on the functionality, taste and/or rheology of the food. Disadvantageously, the preparation of concentrates of active ingredients can be expensive. Furthermore, it is difficult to deliver sufficiently high levels of a range of desired active ingredients without detrimentally affecting the quality of the food.

The present invention, in another aspect, is based on the discovery of a means of delivering active ingredients into certain foodstuffs at levels at which they can provide positive health benefits and/or promote good health. Furthermore, at the same time, the means of delivering the active ingredients can replace ingredients (e.g. fat) in foodstuffs that may potentially be detrimental to good health and contribute positively to the functionality and/or rheology of the foodstuff.

Thus, it is an object of the present invention to provide foodstuffs which may be advantageous over known foodstuffs.

According to a first aspect of the invention, there is provided a method of preparing an aqueous formulation of edible fungi, the method comprising providing a mixture which includes edible fungi in an aqueous liquid and subjecting the mixture to a size reduction process in order to produce an aqueous formulation comprising edible fungal particles having a dimension in a first direction of less than 200 µm, wherein said dimension in said first direction is a maximum dimension of said particles.

Said edible fungi preferably comprise filamentous fungi. Said filamentous fungi preferably comprise fungal mycelia and suitably the edible fungi used in the method includes at least 80 wt %, preferably at least 90 wt %, more preferably at least 95 wt % and, especially, at least 99 wt % of fungal mycelia. Some filamentous fungi may include both fungal mycelia and fruiting bodies. Preferred filamentous fungi for use in the method do not produce fruiting bodies. Where, however, filamentous fungi of a type which produces fruiting bodies are used in the method, the edible fungi used in the method suitably includes at least 80 wt %, preferably at least 90 wt %, more preferably at least 95 wt % of fungal mycelia. Preferably, substantially only the fungal mycelia are used in the method—that is, said edible fungi provided in said mixture preferably do not include any fruiting bodies.

Preferred fungi have a cell wall which includes chitin and/or chitosan. Preferred fungi have a cell wall which includes polymeric glucosamine. Preferred fungi have a cell wall which includes β1-3/1-6-glucans.

The edible fungi may include fungal cells of the order Mucorales as described in WO 00/15045 (DSM).

Said edible fungi is preferably selected from fungi imperfecti.

Preferably, the edible fungi comprise, and preferably consist essentially of, cells of *Fusarium species*, especially of *Fusarium venenatum* A3/5 (formerly classified as *Fusarium graminearum*) (IMI 145425; ATCC PTA-2684 deposited with the American Type Culture Collection, 10801 University Boulevard Manassas, Va., US) as described for example in WO96/21361 (Zeneca) and WO95/23843 (Zeneca).

Edible fungi provided in said mixture are preferably not bound together by a binding agent added to the fungi after they have been grown and/or harvested. Thus, said edible fungi need not be treated with hydrocolloids (e.g. starch, pectin, carrageenan or alginate) and/or with proteins (e.g. milk protein such as casein, ovoprotein such as egg albumin or eggs themselves; vegetable proteins such as soy; cereal proteins, such as gluten; or enzymes such as proteases or phosphodiasterases). It is especially preferred that said edible fungi are not bound together by egg albumin. Thus, said edible fungi need not be texturized prior to inclusion in said mixture.

Edible fungi in said mixture prior to said size reduction process preferably have a dimension in a first direction which is a maximum dimension of particles of said edible fungi, of at least 400 µm. The dimension in said first direction suitably refers to the length of respective edible fungi (especially where the fungi are filamentous). Preferably, the number average dimension in said first direction, e.g. length, of said edible fungi (i.e. the sum of the dimensions in the first direction divided by the total number of fungi measured) in said mixture before said size reduction process is at least 400 µm. The average dimension in said first direction (e.g. length) may be less than 1000 µm, preferably less than 800 µm.

Said mixture may include at least 2% w/w, suitably includes at least 3% w/w, preferably includes at least 5% w/w, more preferably includes at least 9% w/w of said edible fungi on a dry matter basis. Said mixture may include less than 20% w/w, or less than 15% w/w of said edible fungi on a dry matter basis.

Said mixture may include at least 50% w/w, suitably at least 70% w/w. preferably at least 75% w/w, more preferably at least 80% w/w water (including water present in any component of the mixture). In some cases, for example wherein the main or only solid material in the mixture is provided by edible fungi, said water content may be at least 85% w/w or even at least 89% w/w.

The water content is suitably less than 95% w/w, preferably less than 91% w/w. In cases wherein edible fungi are not the only solid material, the water content may be 88% w/w or less.

Said aqueous liquid may comprise water having dissolved and/or suspended solids, for example as in milk, e.g. skim milk, or said aqueous liquid may consist essentially of water. In some embodiments said aqueous liquid may include a protein, for example a vegetable protein such as pea protein isolate. In some embodiments, said aqueous liquid may include a range of ingredients (e.g. sugar, oil, thickener, stabiliser) which may be components of a final product which incorporates said edible fungi. Where said aqueous liquid includes dissolved and/or suspended solids (in addition to said fungi) the amount of such solids in said mixture may be less than 10% w/w, preferably less than 7.5% w/w.

Said mixture may be prepared by contacting said edible fungi and said aqueous liquid. Said edible fungi are preferably in the form of a paste (that is comprising solids and water). The paste may include at least 10% w/w, preferably at least 20% w/w edible fungi (e.g. fungal mycelia or hyphae) on a dry matter basis. The paste may include less than 50%. w/w, preferably less than 40% w/w, more preferably less than 30% w/w of edible fungi on a dry matter basis.

Preferably, after contact of said edible fungi and said aqueous liquid, the edible fungi are allowed to equilibrate with the aqueous liquid for at least 5 minutes, more preferably at least 30 minutes prior to said size reduction process.

Said size reduction process preferably involves the use of a size reduction apparatus which is able to subject the mixture to high shear forces. Said size reduction process suitably does not include the use of a blade or blades arranged solely to affect the cutting of the edible fungi. In one embodiment, the size reduction apparatus may comprise a high shear blender. In another embodiment, said apparatus may comprise a homogeniser. In general, the use of a homogeniser is preferred over the blender. In some embodiments, the size reduction process may use two size reduction apparatuses, suitably operated sequentially. For example, a said blender may be used, followed by a said homogeniser. In some situations, for example when pilot plant (or larger) apparatus is used, shear forces generated within appropriately configured process equipment may be sufficient to effect size reduction.

Preferably, said aqueous formulation prepared is substantially homogenous.

As described above, the aqueous formulation produced in the process comprises particles having a dimension in a first direction of less than 200 µm. The maximum dimension suitably refers to the length of the fungal particles (especially where the fungi are filamentous) but the reference to length is not intended to exclude the possibility of there being two (or more) substantially equal maximum dimensions which may extend perpendicularly to each other. The number average of said first dimensions of solid fungal particles produced in the method is suitably less than 200 µm, is preferably less than 100 µm, is more preferably less than 75 µm and is especially less than 50 µm. In some embodiments, said number average may be less than 40 µm, less than 30 µm or even less than 20 µm. The aforementioned smaller dimensions may be particularly useful for incorporation in certain foodstuffs.

The number average of said first dimensions may be at least 1 µm, preferably at least 5 µm, more preferably at least 10 µm.

Preferably, the ratio of the number average of said first dimensions of the particles after said size reduction to the number average of said first dimensions of the fungi before said size reduction is less than 0.5, preferably less than 0.25, more preferably less than 0.1.

Suitably, the mean of said first dimensions is less than 150 µm, preferably less than 100 µm, more preferably less than 75 µm with a standard deviation on the mean of less than 200 µm, preferably less than 100 µm. The mean is preferably at least 10 µm.

Said edible fungal particles (after said size reduction) may have a dimension in a second direction, measured perpendicular to said first direction, which is suitably less than 20 µm, preferably less than 10 µm, more preferably less than 7 µm and especially 5 µm or less. Said dimension in said second direction is preferably at least 1 µm, more preferably at least 3 µm. Said dimension in said second direction is preferably a diameter of the particles and is preferably substantially the same as a dimension in a third direction, perpendicular to the dimension in said second direction. Thus, preferably said particles have a substantially circular cross-section.

Preferably, the number average of the dimensions of the fungal particles in said second direction is substantially the same for the edible fungi and the particles before and after the size reduction process.

The method of the first aspect may include contacting edible fungi with said aqueous liquid. The edible fungi may be in the form of a hydrated mass (e.g. a paste) which may include at least 50% w/w, suitably at least 60% w/w, preferably at least 70% w/w water. Said hydrated mass suitably includes at least 10% w/w, preferably at least 15% w/w, more preferably at least 20% w/w, especially at least 23% w/w of edible fungi on a dry matter basis. Said amount of edible fungi may be less than 40% W/w, preferably less than 30% w/w on a dry matter basis.

Said aqueous liquid may include at least 80% w/w, preferably at least 90% w/w water. In some embodiments, the aqueous liquid consists essentially of water. In other embodiments, said aqueous liquid may be milk, suitably having less than 15% w/w, preferably less than 10% w/w of milk solids on a dry matter basis. The amount of milk solids may be at least 5% w/w, preferably at least 7.5% w/w on a dry matter basis.

According to a second aspect of the invention, there is provided a method of preparing an aqueous formulation of edible fungi, the method comprising providing a mixture which includes edible fungi in an aqueous liquid and subjecting the mixture to a size reduction process in order to produce an aqueous formulation comprising edible fungal particles having an average aspect ratio of less than 70.

For the avoidance of doubt, the average aspect ratio suitably refers to the average of the dimensions of the fungal particles in a first direction (e.g. the average length) divided by the average of the dimensions of the fungal particles in a second direction (e.g. diameter).

Edible fungi in said mixture prior to said size reduction preferably have an average aspect ratio of at least 100, more preferably at least 150, especially at least 200. The average aspect ratio may be less than 500, preferably less than 300.

The average aspect ratio of the particles after said size reduction process is suitably less than 65, preferably less than 60, more preferably less than 50, especially less than 40. In some embodiments, the average may be less than 30, less than 20, less than 15, less than 10 or even less than 5.

The aspect ratios of the second aspect may be applied to the invention of the first aspect.

According to a third aspect of the present invention, there is provided an aqueous formulation of edible fungi prepared according to the first and/or second aspects.

According to a fourth aspect of the present invention, there is provided an aqueous formulation of edible fungi, the formulation comprising edible fungal particles having a dimension in a first direction of less than 200 µm wherein said dimension in said first direction is a maximum dimension of said particles and/or an aspect ratio of less than 70 in an aqueous liquid.

Said aqueous formulation is preferably substantially homogenous.

Said formulation may includes at least 3% w/w, suitably includes at least 5% w/w, more preferably includes at least 7% w/w and especially includes at least 9% w/w of said edible fungi on a dry matter basis. Said mixture may include less than 20% w/w, or less than 15% w/w of said edible fungi on a dry matter basis.

Said mixture may include at least 50% w/w, suitably at least 70% w/w, preferably at least 75% w/w, more preferably at least 80% w/w water (including water present in any component of the mixture). In some cases, for example wherein the main or only solid material in the mixture is provided by edible fungi, said water content may be at least 85% w/w or even at least 89% w/w.

The water content is suitably less than 95% w/w, preferably less than 91% w/w. In cases wherein edible fungi are not the only solid material, the water content may be 88% w/w or less.

Said formulation optionally includes milk solids (e.g. provided by skim milk). The formulation may include 0 to 15% w/w, suitably 0-10% w/w especially 0 to 7.5% w/w milk solids on a dry matter basis.

Said formulation is suitably shear thinning pseudoplastic, suitably exhibiting apparent viscosities ranging between 3000 and 20 centipoise over the range 2 to 100 rpm on a Brookfield LV1 rotational viscometer.

The aqueous formulation of the fourth aspect may have any relevant characteristic described according to the first and second aspects.

The aqueous formulation described herein may have many potential uses, for example in the preparation of foodstuffs (e.g. yoghurts, deserts, drinks) and/or ingredients for foodstuffs as hereinafter described. Advantageously, the formulation can be used to prepare foodstuffs which have a lower fat content than in corresponding conventional foodstuffs, since the edible fungi when present in the form described have been found to act as a fat mimetic.

One use of the aqueous formulation is in the preparation of dried edible fungal particles having low or substantially no residual moisture. Therefore, according to a fifth aspect of the present invention, there is provided a method of preparing dried particles of edible fungi which suitably may be used as a fat mimetic in downstream applications, the method comprising removing water from an aqueous formulation of the third or fourth aspects and isolating dried particles of said edible fungus.

The dimensions and/or average dimensions and/or aspect ratios of the dried particles are preferably as described herein for the particles in said aqueous formulation.

Dried particles isolated in the method may have a residual moisture content of less than 10% w/w, suitably less than 7.5% w/w, preferably less than 5% w/w, more preferably less than 3% w/w. The residual moisture content may be greater than 0.5% w/w.

The bulk density of the dried particles may be in the range 200-8000 kgm$^{-3}$.

Preferably, water is removed in the method by spray drying the aqueous formulation.

In some circumstances, an aqueous formulation which includes milk, for example skim milk (rather than water alone) together with edible fungal particles may be more advantageously dried than a formulation which does not include milk and/or includes water alone. More particularly, dry particles prepared from a formulation which includes milk may be re-dispersible in an aqueous liquid more readily in downstream processing.

In the method of preparing dry particles, said aqueous formulation used may include at least 5% w/w, preferably at least 7% w/w of edible fungi on a dry matter basis. The amount of edible fungi may be less than 15% w/w, for example less than 13% w/w.

According to a sixth aspect of the invention, there is provided dry particles comprising edible fungi prepared in a method according to the fifth aspect.

According to a seventh aspect of the invention, there is provided dried particles comprising edible fungi per se.

The dimensions and/or average dimensions and/or aspect ratios of the dried particles are preferably as described herein for the particles in the aqueous formulation. In preferred embodiments, the number average of dimensions of fungal particles in a first direction wherein said first dimension is a maximum dimension of the particles is less than 50 μm. The average aspect ratio may be at least 200.

According to an eighth aspect of the invention, there is provided the use of an aqueous formulation comprising edible fungi or dried particles comprising edible fungi as described herein in the preparation of a foodstuff.

According to a ninth aspect of the invention, there is provided a method of preparing a foodstuff, the method comprising contacting an aqueous formulation comprising edible fungi or dried particles comprising edible fungi as described herein with other ingredients of said foodstuff.

The aqueous formulation of edible fungi or dried particles of edible fungi may be as described in any statement herein. The amount of said aqueous formulation or dried particles of said edible fungi may be selected such that in the prepared foodstuff, there is at least 2% w/w, preferably at least 3% w/w, more preferably at least 4% w/w, especially at least 4.5% w/w of edible fungi on a dry matter basis (especially fungal mycelia or hyphae). The amount of said edible fungi on a dry matter basis may be less than 10% W/w, suitably less than 8% w/w, preferably less than 7% w/w, more preferably less than 6% w/w, especially less than 5% w/w.

The other ingredients and the amounts thereof in said foodstuff will generally depend on the nature of the foodstuff being prepared. However, ingredients common to a number of foodstuffs are suitably milk (e.g. skim milk) and/or milk (e.g. skim milk) powder. Thus, the method may involve contacting the edible fungi with milk or milk powder wherein the amount of milk powder may be at least 2% w/w, preferably at least 3% w/w. It is preferably less than 20% w/w, more preferably less than 15% w/w. The amount of skim milk may be less than 80% w/w, preferably less than 75% w/w. Another ingredient that may be common to a number of foodstuffs is sugar (i.e. sucrose) and the method may involve contacting the edible fungi with sugar wherein the amount of sugar is at least 0.5% w/w, suitably is at least 1% W/W preferably is at least 2% w/w, more preferably is at least 3% w/w and, especially, is at least 3.5% w/w. The amount may be less than 15% w/w, preferably less than 13% w/w.

Said foodstuff may include a protein source, especially a vegetable-derived protein source such as pea protein. Such a protein source may be additional to but suitably is used instead of milk or skim milk. Advantageously, the method may involve adding edible fungi or dried particles thereof to a dispersion or preferably a solution, suitably an aqueous solution of said protein, thereby to contact the ingredients. Suitably, the aqueous formulation prepared in the method includes at least 1% w/w, preferably at least 2% w/w, more preferably at least 2.5% w/w, of protein from said protein source; and suitably includes less than 10% w/w, preferably less than 8% w/w, more preferably less than 7% w/w, especially less than 6% W/W of edible fungi on a dry matter basis. Suitably, at least 2% w/w, preferably at least 3% w/w, more preferably at least 4% w/w, especially at least 4.5% w/w of edible fungi on a dry matter basis is in said aqueous formulation.

In some embodiments, said foodstuff may include no milk (dairy product) or skim-milk (dairy product) and, more preferably, includes no ingredient derived from milk. In this event, said foodstuff may advantageously address the problem of lactose intolerance.

It has been found that the edible fungi can act as a fat mimetic and, accordingly, the amount of fat and/or fat containing ingredients added can be reduced. More particularly, it has been found that the edible fungi promote the creamy mouthfeel typically associated with fat.

The foodstuff prepared in the method may be a dessert (e.g. a chilled dessert), for example a mousse, creme caramel or chocolate dessert (or the like). More generally, the foodstuff may be a hot-fill, cold-fill, demouldable, non-demouldable, aerated or non-aerated dessert.

The foodstuff prepared in the method may be a yoghurt. In one embodiment, preparation of a yoghurt may involve contacting, suitably with mixing, edible fungi (suitably in said aqueous formulation or as dry particles) with sugar, milk (e.g. skim milk) and/or milk (e.g. skim milk) powder and water. In another embodiment, preparation of a yoghurt may involve contacting edible fungi (suitably in said aqueous formulation or as dry particles) with a protein source, for example a vegetable-derived protein source such as pea protein. The mixture may be subjected to a size-reduction process; for example sheared. Thereafter, sweetening means, for example sugar may be added. The total protein content in the yoghurt may be at least 2% w/w, preferably at least 3% w/w, more preferably at least 4% w/w, especially at least 5% w/w. The amount may be less than-10% w/w, preferably less than 8% w/w, more preferably less than 6% w/w. After contact and mixing of the ingredients, a culture may be added and the mixture incubated. Thereafter, the mixture may be sheared, prior to the optional addition of flavouring. Advantageously, less than 1% w/w suitably less than 0.5% w/w, preferably less than 0.2% w/w, more preferably less than 0.1% w/w, especially substantially no additional polysaccharide and/or gelatin stabilisers are added to the yoghurt in the method.

The foodstuff prepared in the method may be an ice-cream type dessert. Preparation of a said dessert may involve contacting, suitably with mixing (e.g. with a high shear mixer), said edible fungi with sugar, glucose syrup, milk (e.g. skim milk) powder and oil (e.g. palm oil) and optionally one or more stabiliser/emulsifier. After further treatment, the mixture may be whipped and frozen.

The foodstuff prepared in the method may be a milk drink. In one embodiment, preparation of such a drink preferably involves the use of said edible fungi in combination with milk (e.g. skim milk) paste or powder. For example, the combination may comprise a dispersion of edible fungi in skim milk or a dispersion of dry particles comprising skim milk and fungi. The combination is preferably contacted with other ingredients and milk and/or water added as required with suitable mixing. In another embodiment, a milk drink may be prepared which is not dairy product based and suitably therefore does not include any dairy products. In this case, said foodstuff may be prepared by contacting edible fungi, suitably dry particles thereof, with an oil (e.g. a vegetable oil) and with water. A sweetener for example sucrose may also be added. A suitable stabiliser and/or thickener may be included. The mixture is preferably mixed to produce a substantially homogenous dispersion. Said foodstuff may include at least 1% w/w, preferably at least 2% w/w; and suitably 10% w/w or less, preferably 5% w/w or less of edible fungi on a dry matter basis. Said foodstuff may include at least 0.5% w/w, preferably at least 1% w/w; and suitably less than 5% w/w, preferably less than 2.5% w/w of an oil. The foodstuff may include at least 85% W/W of water.

The foodstuff prepared in the method may be a low fat spread which suitably comprises a water in oil emulsion wherein, suitably, the oil phase is a continuous phase and the water phase is a dispersed phase. Preferably, the foodstuff is prepared such that the edible fungi are a component of the water phase. To this end, preferably the method involves contacting edible fungi, preferably an aqueous dispersion thereof, with other ingredients to prepare the water phase. Preferably, a buttermilk solution is prepared which includes said edible fungi. Said preparation may include a homogenisation step. Other ingredients may be added into the water phase. An oil phase may be prepared in a conventional manner.

After preparation of the respective oil phase and water phase, the two are mixed and processed to prepare the spread.

According to a tenth aspect of the invention, there is provided a foodstuff which comprises edible fungi.

Said edible fungi in said foodstuff may have any feature of the edible fungi prepared in the first and/or second aspects; and/or present in the aqueous formulations of the third and/or fourth aspects and/or resulting from a method according to the ninth aspect.

The ratio of the % w/w of egg albumin powder to the % w/w of edible fungi in said foodstuff is suitably less than 0.1, preferably less than 0.05, more preferably less than 0.01. Preferably the foodstuff includes substantially no albumin powder and/or no egg albumin at all.

Said edible fungi are preferably adapted to act as a fat mimetic in the foodstuff.

Said foodstuff preferably includes a quantity of edible fungi on a dry matter basis as present in the foodstuff prepared in the ninth aspect. Said foodstuff may include 2-10% w/w, preferably 4-10% w/w of edible fungi on a dry matter basis.

Said foodstuff preferably includes edible fungal particles having a dimension in a first direction of less than 200 μm wherein said dimension in said first direction is a maximum dimension of said particles and/or an aspect ratio of less than 70. The dimensions and/or aspect ratio may be as described in any statement herein.

Said foodstuff may be a dairy product.

Said foodstuff may be selected from the group comprising a dessert (e.g. yoghurt or ice-cream type dessert), milk drink (including non-dairy based drinks) or low-fat spread. Preferably, it is selected from a dessert (e.g. yoghurt or ice-cream type dessert) and a low-fat spread.

When said foodstuff is a yoghurt, it may have any feature of the yoghurt described according to the ninth aspect.

When said foodstuff is an ice-cream type dessert, it may have any feature of the dessert described according to the ninth aspect.

When said foodstuff is a milk drink, it may have any feature of the drink described according to the ninth aspect.

When said foodstuff is a low fat spread, it may have any feature of the spread described according to the ninth aspect.

According to an eleventh aspect of the invention, there is provided the use of an edible fungus in the preparation of a foodstuff for human consumption, especially a dairy product (suitably so that said edible fungus, not solely an extract thereof is present in the foodstuff), for treatment of joint mobility disorders; for reducing fat uptake; for lowering cholesterol; for immune function stimulation; as a pre-biotic and/or for affecting satiety. According to a twelfth aspect of the invention, there is provided a method of preparing a foodstuff, especially a dairy product, having at least 300 mg (preferably at least 350 mg and suitably less than 600 mg) of N-acetylglucosamine per 100 g of foodstuff; at least 600 mg (preferably at least 750 mg and suitably less than 1300 mg) of β-glucan per 100 g of foodstuff.

The edible fungi and/or foodstuff of the eleventh and/or twelfth aspects may be as described in any statement herein. Preferably, said edible fungi is adapted to act as a fat mimetic in said foodstuff.

Said foodstuff is preferably fluidic and/or spreadable.

Said foodstuff suitably includes less than 2% w/w, preferably less than 0.5% w/w, especially less than 0.25% w/w or even less than 0.1% w/w of egg albumin. Said, foodstuff preferably includes substantially no egg albumin.

Said edible fungi preferably comprise a filamentous fungus.

According to a thirteenth aspect, there is provided a foodstuff, having at least 300 mg of N-acetylglucosamine and at least 600 mg of β-glucan per 100 g of foodstuff.

Any feature of any aspect of any invention or embodiment described herein may be combined with any feature of any aspect of any other invention or embodiment described herein mutatis mutandis.

Specific embodiments of the invention will now be described, by way of example, with reference to the accompanying drawings, in which.

The following are referred to hereinafter:

mycoprotein paste—refers to a visco-elastic material comprising a mass of edible filamentous fungus derived from *Fusarium venenatum* A3/5 (formerly classified as *Fusarium graminearum* Schwabe) (IMI 145425; ATCC PTA2684 deposited with the American type Culture Collection, 10801 University Boulevard Manassas, Va., US) and treated to reduce its RNA content to less than 2% by weight by heat treatment. Further details on the material are provided in WO96/21362 and WO95/23843. The material may be obtained from Marlow Foods Limited of Stokesley, U.K. It comprises about 25 wt % solids made up of non-viable RNA reduced fungal hyphae of approximately 400-750 μm length, 3-5 μm in diameter and a branching frequency of 2-8 tips per hyphal length.

Hobart mixer—a beater mixer with a planetary mixing action made by Hobart Corporation of Troy Ohio, U.S.A.

Silverson L4RT high shear blender—obtained from Silverson Machines Ltd of Bucks, England.

APV Lab 2000 homogeniser—supplied by APV Homogenisers AS of Denmark. It is a research and development tool for exploring homgenisation at feed stream pressures of up to 2000 bar.

Crepaco homogeniser—supplied by APV Crepaco and capable of operating at a maximum feed stream pressure of 350 bar.

Kestner Lab Spray Dryer—Spray Dryer No 5 obtained from Kestner Evaporator & Engineer Co of London, England.

Stefan Mixer—supplied by Stephan Nahrungsmittel und Verfahrens Technik of Germany. For this mixer, the mixing head is based on the speed of rotation of selected blade designs.

Modified starch (National Starch Coarse Instant Clear Jel)—a pre-gelatinised modified starch used as a thickener obtained from National Starch.

Butter flavour 2807—a mixture of flavouring substances obtained from Danisco Ingredients of Denmark.

Buttermilk powder—supplied by Diary Crest of Surbiton, U.K.

Pea protein isolate—obtained from ACP Ingredients Limited

Oil blend (Grindstead PS209)—blend of mono and triglycerides based on edible fully hydrogenated vegetable oil obtained from Danisco Ingredients of Denmark.

Ytron mixer—a high shear mixer

Dimodan OT—an emulsifier comprising distilled monoglycerides of fatty acids supplied by Danisco Ingredients of Denmark.

Pectin Grinsted PS209—a pectin thickener from Danisco.

Butter flavour 2822—a mixture of flavouring substances obtained from Danisco Ingredients of Denmark.

Crepaco Scraped Surface Heat Exchanger—supplied by APV Crepaco. It provides a means by which product can be heated or cooled within a jacketed vessel and, at the same time, scraping the surface of the heat transfer contact point so as to prevent fouling.

Genupectin YM-100-L—a pectin thickener obtained from CP Kelco UK Ltd

Viscarin GP2050—a carrageenan—based hydrocolloid obtained from FMC Biopolymer Ltd.

EXAMPLE 1

The Influence of Dispersion Time and Mixing Methodology on Dispersion Efficiency Mycoprotein paste was added to shop-bought skim milk at 25% w/w and left to 'hydrate' further for 5, 15 and 30 minutes. After each time interval the 'dispersion' was filtered using a coarse muslin cloth and the amount of residual solids quantified as a measure of degree of dispersion. In addition, at each time interval one batch of the dispersion was mixed for 4 minutes using a Hobart mixer on setting number 4 whilst a second batch was mixed using a Silverson L4RT high shear blender using a slotted disintegrating head at 8000 rpm. In each case the dispersion efficiency was measured on the basis of residual solids in the muslin cloth.

Results are provided in Table 1.

TABLE 1

| PROCESS | TIME (min) | % RESIDUAL SOLIDS |
| --- | --- | --- |
| NO TREATMENT | 5 | 95% |
|  | 15 | 94% |
|  | 30 | 94% |
| MIXING USING | 5 | 20% |
| SILVERSON MIXER | 15 | 15% |
|  | 30 | 8% |
| MIXING USING | 5 | 60% |
| HOBART MIXER | 15 | 42% |
|  | 30 | 30% |

The experiments illustrate that it is beneficial to hydrate the mycoprotein paste prior to dispersion by agitation. Additionally, it is beneficial to use a high shear mixer (e.g. Silverson). Similar benefits were found for dispersions made in either 3% w/w caseinate solution or 3% w/w whey protein concentrate instead of skim milk. In general terms, any protein-containing aqueous liquid may be used.

Unless otherwise stated herein, when a formulation comprising mycoprotein paste and skim milk or water is used, the paste is allowed to hydrate for 30 minutes prior to subsequent use.

EXAMPLE 2

Investigations Relating to Homogenisation

Figure 1:
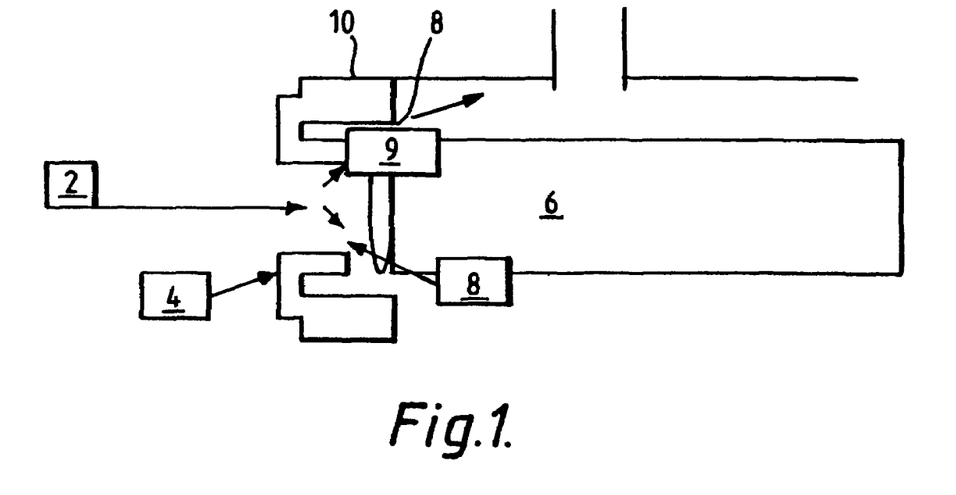
FIG. 1 is a schematic representation of an APV Lab 2000 homogeniser.

The basic principles of homogenisation will be described with reference to FIG. 1. Unhomogenised product 2 enters the valve seat 4 at low viscosity and low pressure. As the product flows through an adjustable close clearance area between a valve 6 and seat 4, there is a rapid increase in velocity with a corresponding decrease in pressure. This intense energy transition occurs in microseconds and produces turbulent three dimensional mixing layers that disrupt particles at the discharge from the gap 8. The homogenised product (9) impinges on an impact ring 10 and exists at a pressure sufficient for movement to the next processing stage. The acceleration of the liquids through the gap also produces a pressure drop to below the vapour pressure of some components. This may lead to implosive forces being generated.

Effect of Homogenisation Temperature on Flowrate through Homogeniser

The effect of homogenisation temperature on flow rate through the APV Lab 2000 homogeniser of the mycoprotein/skim milk formulation described in Example 1 was assessed over a range of pressures and the results are provided in Table 2 wherein "$1^{st}$ stage" and "$2^{nd}$ stage" pressure refer to the pressure of the formulation when entering through valve seat 4 and the subsequent downstream pressure (the pressure measured at the exit of the valve assembly) respectively.

TABLE 2

| Temperature °C. | $2^{nd}$ stage pressure (bar) | $1^{st}$ stage pressure (bar) | Q (kg/h) |
|---|---|---|---|
| 20 | 0 | 0 | 15 |
| 20 | 90 | 500 | 8 |
| 20 | 230 | 1210 | 6 |
| 20 | 350 | 1600 | 5.4 |
| 50 | 90 | 500 | 11 |
| 50 | 230 | 1210 | 10 |
| 50 | 350 | 1600 | 10 |
| 70 | 90 | 500 | 8 |
| 70 | 230 | 1210 | 6.6 |
| 70 | 350 | 1600 | 6 |

It will be noted from Table 2 that the optimum flow rate is achieved at about 50° C.

(b) Effect of Dispersion and/or Homogenisation Processes on Hyphal Aspect Ratio of the Mycoprotein Typically, mycoprotein hyphae are 400-750 μm in length with a diameter of 3-5 μm. The effect of a range of dispersion and/or homogenisation processes on the measured hypal lengths of mycoprotein filaments was investigated. Details of processes used and the results are provided in Table 3a. In each case, a formulation was prepared of mycoprotein paste (25% w/w) and water or skim milk, with the paste being allowed to hydrate for 30 minutes prior to the subsequent processes described in the Table.

The assessment of hyphal lengths in a sample of mycoprotein is undertaken as follows: Light microscope preparations are made from the sample and light microscope images captured and processed as greyscale bitmaps. The images are saved on 8-bit greyscale bitmaps to a resolution of 764-576 pixels. The magnification was determined as 0.81 micron/pixel using a static graticule and corresponding to a field of view of 0.62×0.47 mm for each image. Dedicated software was written to analyse the images.

TABLE 3a

| Example No | Process | Mean (um) | Standard deviation (um) | Median (um) |
|---|---|---|---|---|
| 2a | The formulation of mycoprotein paste in water was dispersed using a Silverson blender as described in Example 1 | 34.1 | 66.1 | 7.3 |
| 2b | The formulation of mycoprotein paste in water was dispersed using a Silverson blender as described in Example 1 followed by homogenisation using the Crepaco homogeniser at 270 bar | | | |
| 2c | The formulation of mycoprotein paste in water was dispersed using a Silverson blender as described in Example 1 followed by homogenisation using the Crepaco homogeniser at 270 bar followed by homogenisation using the APV Lab 2000 homogeniser at an inlet pressure of 750 bar and a second stage pressure of 75 bar | 18.3 | 20.5 | 12.1 |
| 2d | The formulation of mycoprotein paste in water was dispersed using a Silverson blender as described in Example 1 followed by homogenisation using the Crepaco homogeniser at 270 bar followed by homogenisation using the APV Lab 2000 homogeniser at an inlet pressure of 1500 bar and a second stage pressure of 350 bar. | 15.7 | 15.7 | 11.3 |
| 2e | The formulation of mycoprotein paste in skim milk was dispersed using a Silverson blender as described in Example 1. | 50.8 | 53.1 | 31.5 |
| 2f | The formulation of mycoprotein paste in skim milk was dispersed using a Silverson blender as described in Example 1 followed by homogenisation using the Crepaco homogeniser at 270 bar. | 26.5 | 52.2 | 13.7 |
| 2g | The formulation of mycoprotein paste in skim milk was dispersed using a Silverson blender as described in Example 1 followed by homogenisation using the Crepaco homogeniser at 270 bar followed by homogenisation using the APV Lab 2000 homogeniser at an inlet pressure of 750 bar and a second stage pressure of 75 bar. | 15.9 | 14.9 | 11.3 |
| 2h | The formulation of mycoprotein paste in skim milk was dispersed using a Silverson blender as described in Example 1 followed by homogenisation using the Crepaco homogeniser at 270 bar followed by homogenisation using the APV Lab 2000 homogeniser at 1500 bar. | 15.4 | 13.5 | 11.3 |

It will be noted from Table 3a that the Silverson and/or the APV or Crepaco homogenisers can be used to reduce the aspect ratio (length/diameter) of the mycoprotein filaments significantly—from 90 to about 10 for the Silverson; to about 5 in the case of the Crepaco homogeniser; and to about 3 in the case of the APV homogeniser (assuming the mean native filament length to be 450 μm and 5 μm in diameter).

EXAMPLE 3

Spray Drying of Homogenised Dispersion of Mycoprotein

Dispersions of mycoprotein paste in water (Example 3a) or skim milk (Example 3b) were prepared as described in Example 1 except that each dispersion was made at 30% w/w and was homogenised using an APV Crepaco homogeniser at 270 bar before spray drying. Spray drying was carried out using a Kestner Lab Spray Drier at 190° C. inlet and 90° C. outlet temperature and an evaporation rate of 25 Kg/L. In addition, a further sample (Example 3c) was prepared by further homogenising the aforementioned sample in skim milk on the APV Lab 2000 machine (using inlet pressure of 1500 bar and outlet pressure of 300 bar) before spray drying as described.

The typical morphology of the spray dried material was assessed as described in Example 2(b) and the results are provided in Table 3b.

TABLE 3b

| Example No | Summary of Process | Mean (um) | Standard deviation (um) | Median (um) |
|---|---|---|---|---|
| 3a | Mycoprotein in water homogenised at 270 bar and then spray dried. | 29.3 | 36.8 | 15.4 |
| 3b | Mycoprotein in skim milk homogenised at 270 bar and then spray dried | 23.6 | 37.2 | 12.1 |
| 3c | Mycoprotein in skim milk homogenised at 270 bar, then at 1500 bar and then spray dried. | 14.9 | 12.3 | 12.1 |

EXAMPLE 4

Preparation and Evaluation of Yoghurts

Seven batches of yoghurt were prepared such that a mycoprotein paste content of 20% w/w was present in the final product. This concentration delivers about 5% W/W of paste solids on a dry matter basis. The seven batches varied from one another in using various hyphal aspect ratios and/or dispersion rheologies (based on the results in Example 1) and some were made using dried product produced as described in Example 3.

In a separate experiment, a batch of yoghurt was prepared such that the mycoprotein paste content of 20% w/w was present in the final product. However, instead of skim milk protein a non-dairy protein was used. This was pea protein isolate (itself containing about 85% protein).

Details on the preparation of mycoprotein for the batches are provided in Table 4.

TABLE 4

| Example No | Description |
|---|---|
| 4a | Control with protein at 5.5% w/w (No mycoprotein). |
| 4b | 20% w/w mycoprotein addition using formulation of mycoprotein in water, dispersed by Silverson mixing (Example 1a). |
| 4c | 20% w/w mycoprotein addition using formulation of mycoprotein in water, homogenised with a Crepaco unit at 270 bar (Example 2b) |
| 4d | 20% w/w mycoprotein addition using formulation of mycoprotein in water and homogenised with APV Lab 2000 at 750 bar (similar to Example 2c but Crepaco not used). |
| 4e | 20% w/w mycoprotein addition using formulation of mycoprotein in water, homogenised with an APV Lab 2000 at 1750 bar (similar to Example 4d but higher pressure used) |
| 4f | Yoghurt prepared from reconstituted mycoprotein and skim milk spray dried power, so as to give an equivalent of 20% w/w native paste in the finished product. Powder prepared using a Crepaco homogeniser at 270 bar followed by spray drying as described in Example 3b |
| 4g | Yoghurt prepared from reconstituted mycoprotein and skim milk spray dried powder, so as to give an equivalent of 20% w/w native paste in the finished product. Powder prepared using an APV Lab 2000 homogeniser at 1750 bar followed by spray drying. |
| 4h | 20% w/w mycoprotein addition using formulation of mycoprotein in 3% (w/w)_pea protein solution, homogenised with an APV Lab 2000 at 750 bar |

The yoghurts of Examples 4a-4g were prepared as a base mix to which strawberry fruit preparation (obtained from Kerry Aptunion Fruit Preparations of Worcester, England) was added. The base mixes included sugar, skim milk, skim milk powder and water at levels described in Table 5, with the total protein content in each case being about 5.5% w/w.

TABLE 5

| Batch No | Mycoprotein/ protein used | Paste/spray dried powder (%) | Skim Milk (%) | Skim Milk Powder (%) | Sugar (%) | Water (%) |
|---|---|---|---|---|---|---|
| 4.1 | 4a | 0 | 80 | 8.17 | 4 | 7.83 |
| 4.2 | 4b | 20 | 71 | 2.74 | 4 | 2.26 |
| 4.3 | 4c | 20 | 71 | 2.74 | 4 | 2.26 |
| 4.4 | 4d | 20 | 71 | 2.74 | 4 | 2.26 |
| 4.5 | 4e | 20 | 71 | 2.74 | 4 | 2.26 |
| 4.6 | 4f | 10.4 | 20 | 2.57 | 4 | 63.03 |
| 4.7 | 4g | 10.4 | 20 | 2.57 | 4 | 63.03 |

In the case of the pea protein yoghurt, pea protein isolate was dissolved in water at 3.1% w/w protein content in the final solution. Mycoprotein was then dispersed in this at 20% w/w and the resultant dispersion homogenized using the APV Lab Machine at 750 bar. Sugar was added at 6% w/w and the resultant base mix was processed by fermentation to yoghurt as described below.

The base mixes prepared were heated with agitation to 90° C. for 10 minute and then cooled rapidly to 42° C. A mixed thermophilic blend of culture was added at a rate of 0.1 units per litre where 1 unit=about 1 gram of freeze dried culture of *Lactobacillus delbrueckii* ssp *bulgaricus, Streptococcus themophillus, Lactobacillus acidophilus* and *Bifidobacterium*. The mixes were incubated at 42° C. for approximately 6 hours or until the pH had dropped from 6.8 to 4.55. At this end point, the incubating mixes were sheared using a hand held Braun™ high shear blender. The sheared mixes were then cooled to <20° C. where fruit preparation was added at 15% w/w and the mixes potted and lidded with cooling to <5° C. The pots were equilibrated for six days prior to evaluation.

No additional polysaccharide or gelatin stabilisers were used. Finished-product fat levels for Batches 2 to 8 were <0.5% w/w.

Samples of yoghurts were evaluated to assess the geometry of the mycoprotein filaments contained therein as is described in Example 2(b) and the results are provided in Table 6.

TABLE 6

| Batch No used for yoghurt preparation | Mean (um) | Standard deviation (um) | Median (um) | 25th percentile (um) | 75th percentile (um) | Mean from log scale (um) |
|---|---|---|---|---|---|---|
| 4.2 | 18.7 | 36.5 | 7.3 | 4.0 | 13.3 | 7.7 |
| 4.3 | 10.0 | 17.9 | 5.7 | 3.2 | 9.7 | 5.6 |
| 4.4 | 13.9 | 17.2 | 8.9 | 4.8 | 16.2 | 8.5 |
| 4.5 | 12.4 | 10.9 | 8.9 | 5.7 | 15.4 | 8.8 |
| 4.6 | 15.0 | 29.7 | 8.1 | 4.8 | 12.1 | 7.8 |
| 4.7 | 16.0 | 27.8 | 8.1 | 4.8 | 15.4 | 9.0 |

The yoghurts prepared were evaluated by a panel of assessors trained in sensory descriptive analysis. A vocabulary was agreed during pretrial training sessions with this panel such that textural attributes for the yoghurts could be assessed and quantified. The scores for attributes assessed and overall score for acceptability are provided in Table 7a. The higher the value for acceptability, the more acceptable the product.

TABLE 7a

| Batch No used for yoghurt preparation | Smooth | Grainy | Soft | Airy | Watery | Chalky | Acceptability |
|---|---|---|---|---|---|---|---|
| 4.1 | 9 | 2 | 2 | 8 | 7 | 2 | 5 |
| 4.2 | 2 | 9 | 6 | 9 | 4 | 6 | 2 |
| 4.3 | 2 | 8 | 6 | 9 | 4 | 9 | 2 |
| 4.4 | 9 | 2 | 7 | 9 | 2 | 2 | 7 |
| 4.5 | 9 | 3 | 7 | 9 | 2 | 3 | 6 |
| 4.6 | 6 | 6 | 8 | 9 | 5 | 9 | 3 |
| 4.7 | 8 | 4/5 | 8 | ? | 5 | 8 | 5 |
| 4.8 | 9 | 2 | 3 | 8 | 6 | 6 | 5 |

Table 7a shows that the smoothness of the product is significantly affected by the process used to prepare the mycoprotein for the yoghurt. Higher pressure homogenisation tends to lead to smoother yoghurts. Accordingly, in preferred embodiments for preparing yoghurts, high pressure homogenisation is used and/or the mean hyphal length is reduced to about 15 μm.

The yoghurt made from pea protein was found to process to give an acceptable product. The pea protein had been selected as a non-dairy protein source which did not have significant undesirable flavours associated with it, so often a characteristic of products of this type. The resultant product was found to have good eating quality as described by Table 7a. In particular, the use of pea protein with mycoprotein was found to give a good flavour profile which is potentially a significant product advantage where off-flavours such as "beany" are often associated with products of this type. It should be appreciated from the examples that the mycoprotein appears to behave as a fat mimetic importing good mouth feel. Further, it is not essential to use additional polysaccharides or gelatin to promote texture at the very low fat levels found.

As described above, the mycoprotein paste content in the products was 20% w/w and/or the products included about 5% w/w of paste solids. At this level, it is believed sufficient glucosamine, chitin and β-Glucan can be delivered to have positive health benefits. For example, 1.5 g/day of glucosamine, 3-10 mg/day of β-glucans, 1 g/day of chitin and a ratio of linoleic acid to linolenic acid in the range 4.1 to 10.1 may be desirable.

Table 7b details nutrient levels supplied by mycoprotein in a 150 g pot of yoghurt of various paste inclusions (%) and paste g wet wt.

TABLE 7b

| | | Nutrient from mycoprotein | | | | | | |
|---|---|---|---|---|---|---|---|---|
| Paste Inclusion (% w/w) | Paste (g wet wt) | Glucosamine (mg) | Chitin (mg) | B-Glucan (mg) | Fibre (g) | Fat (g) | w-3-lin (mg) | w-6-lin (mg) |
| 10 | 15 | 300 | 300 | 600 | 0.900 | 0.003 | 60.0 | 206 |
| 15 | 22.5 | 450 | 450 | 900 | 1.350 | 0.005 | 90.0 | 309 |
| 20 | 30 | 600 | 600 | 1,200 | 1.800 | 0.006 | 120.0 | 411 |
| 25 | 37.5 | 750 | 750 | 1,500 | 2.250 | 0.008 | 150.0 | 514 |
| 30 | 45 | 900 | 900 | 1,800 | 2.700 | 0.009 | 180.0 | 617 |

As will be appreciated from the above, preparing yoghurts in the manner described enables advantageously high levels of important nutrients to be supplied whilst not affecting significantly (and in some cases improving) the eating quality of the yoghurt.

EXAMPLE 5

Preparation and Evaluation of Ice-Cream Type Desserts

Eight batches of ice-cream type dessert were prepared such that a mycoprotein content of 20% w/w was present in the final product. This concentration delivers about 5% w/w of paste solids. The eight batches varied from one another in using various hyphal aspect ratios and/or dispersion rheologies and some were made using dried product produced as described in Example 3. Details of the batches and particularly the preparation of the mycoprotein in the batches are provided in Table 8.

TABLE 8

| Example No | Description |
| --- | --- |
| 5a | Control without extra skim milk to compensate for paste (no mycoprotein) |
| 5b | Control with extra skim milk to compensate for paste (no mycoprotein) |
| 5c | 20% w/w mycoprotein addition using formulation of mycoprotein in water, dispersed by Silverson mixing (Example 2a) |
| 5d | 20% w/w mycoprotein addition using formulation of mycoprotein in water homogenised with a Crepaco unit at 270 bar (Example 2b) |
| 5e | 20% w/w mycoprotein addition using formulation of mycoprotein in water homogenised with an APV Lab 2000 at 1750 bar (similar to Example 2c but Crepaco not used). |
| 5f | 20% w/w mycoprotein addition using formulation of mycoprotein in water, homogenised with an APV Lab 2000 at 1750 bar (similar to Example 5e but higher pressure used). |
| 5g | Dessert prepared from reconstituted mycoprotein and skim milk spray dried powder, so as to give an equivalent of 20% w/w native paste in the finished product. Powder prepared using a Crepaco homogeniser at 270 bar as pre-treatment. |
| 5h | Dessert prepared from reconstituted mycoprotein and skim milk spray dried powder, so as to give an equivalent of 20% w/w native paste in the finished product. Powder prepared using an APV Lab 2000 homogeniser at 1750 bar as pre-treatment. |

All desserts were prepared as having finished product fat levels of 4.5% w/w and 31% w/w total solids. A summary of the ingredients is provided in Table 9.

TABLE 9

| Batch No | Mycoprotein/ protein used | Water % w/w | Skim milk powder % w/w | Glucose syrup % w/w | Sugar % w/w | Palm oil % w/w | Stabiliser Emulsifier % w/w |
| --- | --- | --- | --- | --- | --- | --- | --- |
| 5.1 | 5a | 69 | 9 | 5 | 12 | 4.5 | 0.5 |
| 5.2 | 5b | 63.8 | 14.2 | 5 | 12 | 4.5 | 0.5 |
| 5.3 | 5c | 69 | 9 | 5 | 12 | 4.5 | 0.5 |
| 5.4 | 5d | 69 | 9 | 5 | 12 | 4.5 | 0.5 |
| 5.5 | 5e | 69 | 9 | 5 | 12 | 4.5 | 0.5 |
| 5.6 | 5f | 69 | 9 | 5 | 12 | 4.5 | 0.5 |
| 5.7 | 5g | 10.4# | 3.6 | 5 | 12 | 4.5 | 0.5 |
| 5.8 | 5h | 10.4# | 3.6 | 5 | 12 | 4.5 | 0.5 | i.e. 10.4% w/w powder (skim milk and mycoprotein) plus 64% w/w water giving a total of 74.4% w/w water and powder.

The homogenised dispersion of mycoprotein in water (or reconstituted powder) was heated to 50° C. along with the dry ingredients, glucose syrup and oil. This heated mix was then mixed using the Silverson at 8000 rpm, allowing the temperature to increase to 80° C. and holding for 30 seconds prior to rapid cooling to below 10° C. This mix was then 'aged' for four hours before whipping and freezing using a Gaggio laboratory ice cream maker.

Samples of each dessert were evaluated to assess the geometry of the mycoprotein filaments contained therein and the results are provided in Table 10.

TABLE 10

| Batch No | Mean (um) | Standard deviation (um) | Median (um) |
| --- | --- | --- | --- |
| 5.3 | 23.5 | 42.5 | 11.3 |
| 5.4 | 16.0 | 22.0 | 11.3 |
| 5.5 | 15.6 | 15.2 | 11.3 |
| 5.6 | 17.5 | 17.8 | 12.9 |
| 5.7 | 22.2 | 30.1 | 12.1 |
| 5.8 | 19.2 | 17.7 | 13.7 |

The desserts prepared were evaluated by a panel of assessors trained in sensory descriptive analysis as for Example, 4 above. The raw scores obtained were converted into a principal components plot which is provided in FIG. 2.

Acceptability scores for the desserts are shown in Table 11a on a scale wherein 0 represents "acceptable no defects" up to 3 which represents "unacceptable". Table 11 shows each to have a score of less than 1 and, therefore, each is "acceptable".

TABLE 11

| Example No | Score |
| --- | --- |
| 5a | 0 |
| 5b | 0 |
| 5c | 0.1 |
| 5d | 0.4 |
| 5e | 0.4 |
| 5f | 0.2 |
| 5g | 0.9 |
| 5h | 0.2 |

As will be appreciated, the mycoprotein replaces fat in the dessert and yet the eating quality of the dessert is acceptable. Thus, the mycoprotein appears to act as a fat mimetic.

Figure 2:
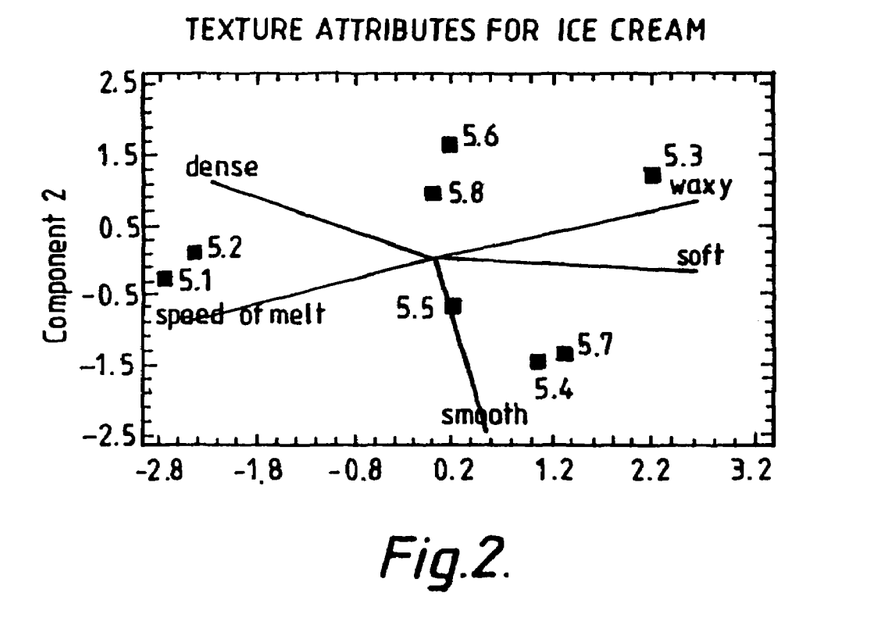
FIG. 2 is a principal component plot describing the attributes of an ice-cream type dessert.

Additionally, referring to FIG. 2, the controls (Examples 5a and 5b) are separated from those containing mycoprotein chiefly by speed of melt (in the mouth). Thus, the mycoprotein appears to affect the freeze-thaw characteristics of the dessert.

As for the yoghurt, the mycoprotein paste content in the desserts was 20% w/w and/or the desserts included 5% w/w of paste solids. The nutrient levels may be calculated based on details in Table 7b on the basis of, for example two conventional scoops (about 150 ml or 100 g).

Preparing desserts in the manner described enables advantageously high levels of important nutrients to be supplied whilst not affecting significantly the eating quality.

EXAMPLE 6

Preparation and Evaluation of Flavoured Milk Drinks

Seven batches of flavoured milk drink were prepared such that a mycoprotein paste content of 18.75% w/w was present in the final product. This concentration delivers about 4.70% w/w of paste solids. The seven batches varied from one another in using various hyphal aspect ratios and/or dispersion rheologies (based on the results in Example 1) and some were made using dried product produced as described in Example 3.

Details of the batches and particularly the presentation of mycoprotein in the batches are provided in Table 12.

TABLE 12

| Example No | Description |
|---|---|
| 6a | Control using skim milk (no mycoprotein) |
| 6b | 18.75% w/w mycoprotein addition using formulation of mycoprotein in skim milk dispersed by Silverson mixing (Example 2a) |
| 6c | 18.75% w/w mycoprotein addition by using formulation of mycoprotein in skim milk, and homogenised with a Crepaco unit at 270 bar (Example 2d) |
| 6d | 18.75% w/w mycoprotein addition by using formulation of mycoprotein in skim milk, homogenised with an APV Lab 2000 at 750 bar (similar to Example 2c but Crepaco not used). |
| 6e | Flavoured milk drink prepared from reconstituted mycoprotein and skim milk spray dried powder, so as to give an equivalent of 20% w/w native paste in the finished product. Powder prepared using a Crepaco homogeniser at 270 bar as pre-treatment. |
| 6f | Flavoured milk drink prepared from reconstituted mycoprotein and skim milk spray dried powder, so as to give an equivalent of 18.75% w/w native paste in the finished product. Powder prepared using an APV Lab 2000 homogeniser at 1750 bar as pre-treatment. |
| 6g | 18.75% w/w mycoprotein by mixing mycoprotein in skim milk using a Stefan mixer then homogenised on a dairy homogeniser at 200 bar and then processed on a UHT plant at 140° C. for 4 seconds then cooled at 5° C. and packed into 250ml Tetra Paksm cartons. |

A summary of the ingredients in the milk drinks is provided in Table 13.

TABLE 13

| Batch No | Mycoprotein/ protein used | Paste/spray dried powder % w/w | Skim Milk % w/w | Skim Milk with Paste % w/w | Skim Milk with powder % w/w | Sugar % w/w | Stabiliser % w/w | Flavour and colour % w/w | Water % w/w |
|---|---|---|---|---|---|---|---|---|---|
| 6.1 | 6a | 0 | 93.75 | 0 | 0 | 6 | 0.03 | 0.24 | 0 |
| 6.2 | 6b | 0 | 0 | 93.75 | 0 | 6 | 0.03 | 0.24 | 0 |
| 6.3 | 6c | 0 | 0 | 93.75 | 0 | 6 | 0.03 | 0.24 | 0 |
| 6.4 | 6d | 0 | 0 | 93.75 | 0 | 6 | 0.03 | 0.24 | 0 |
| 6.5 | 6e | 9.04 | 0 | 0 | 2.41 | 6 | 0.03 | 0.24 | 82.28 |
| 6.6 | 6f | 9.04 | 0 | 0 | 2.41 | 6 | 0.03 | 0.24 | 82.28 |
| 6.7 | 6g | 0 | 0 | 93.75 | 0 | 6 | 0.03 | 0.24 | 0 |

Batch numbers 6.1 to 6.4 were prepared by adding sugar, stabiliser, colour and flavour to either skim milk (batch number 6.1) or skim milk and paste (batch numbers 6.2 to 6.4). The mixtures were then heated up to 95° C., held for 1 minute and then cooled to less than 10° C.

Batch numbers 6.5 and 6.6 were prepared by reconstituting the skim milk and paste powder in water then adding sugar, stabiliser, colour and flavour. The mixtures were then heated up to 95° C., held for 1 minute and then cooled to less than 10° C.

Batch number 6.7 was prepared by mixing mycoprotein in skim milk using a Stefan mixer, homogenising the mixture using a diary homogeniser at 200 bar, adding sugar, stabiliser, colour and flavour and then processing on a UHT plant at 140° C. for 4 seconds, followed by cooling to 5° C. and packing into 250 ml Tetra Paks™ cartons.

The milk drinks were assessed by a panel as described in the preceding examples. Results are shown in Table 14a.

TABLE 14a

| Batch No | Drinking Quality |
|---|---|
| 6.1 | Thin body lacking in creaminess; good colour and flavour. |
| 6.2 | Thick pulpy texture; good colour and flavour. |
| 6.3 | Not as pulpy as Batch No. 6.2; good colour and flavour. |
| 6.4 | Good thick smooth texture; creamy; good colour and flavour. |
| 6.5 | Similar to batch no. 6.3 but lacking slightly in body. |
| 6.6 | Similar to batch no. 6.4 but lacking slightly in body. |
| 6.7 | Initially good creaminess, colour and flavour although on storage, went very thick and pulpy and started to separate. The sample was too thick which affected seals on the TetraPack ™ carton and meant that the product had to be stored at below 5° C. and had a shorter shelf life compared to that of UHT milk products. |

The mycoprotein replaces fat in the drink and the eating quality is still acceptable. Thus, the mycoprotein appears to act as a fat mimetic.

The mycoprotein paste content in the drinks was 18.75% w/w and/or the drinks included 4.70% w/w of paste solids. The nutrient levels may be calculated based on details in Table 7b.

Preparing drinks in the manner described enables advantageously high levels of nutrients to be supplied whilst not affecting significantly the eating quality.

EXAMPLE 7

Preparation and Evaluation of Non-dairy Milk Alternative using Mycoprotein

Dry ingredients were mixed together and dispersed with oil into water using a Silverson mixer at about 8000 rpm for 10 minutes. The resultant mix was heated in a a bain-marie to 90° C. for 5 minutes and then cooled to 4° C. with further shearing using a Silverson mixer again at 8000 rpm for 10 minutes. The dispersion was then homogenised using an APV Lab homogeniser at 1000 bar. The formulation used is shown below:

| Ingredient | % w/w |
|---|---|
| Sucrose | 1.000 |
| Frozen mycoprotein paste | 10.000 |
| Sunflower Oil | 1.500 |
| Genupectin YM-100-L | 0.325 |
| Viscarin GP 2050 | 0.025 |
| Water to | 100.000 |

The product was evaluated by trained assessors alongside commercially available non-dairy milk alternatives and was found to perform at parity in terms of texture but with superior flavour delivery due to the inherently bland taste profile of mycoprotein. This is a significant product advantage. The product may address the problem of lactose intolerance whilst not being soy protein based.

EXAMPLE 8

Preparation and Evaluation of Low Fat Spreads

A low fat spread is a water in oil emulsion where the oil phase is the continuous phase and the water phase is the dispersed phase, wherein an emulsifier or emulsifiers is/are used to prevent the two phases from separating.

Preparation of Water Phase
This comprised the following:

|  | % w/w |
|---|---|
| Mycoprotein paste & BMP solution | 58.39 |
| Salt | 1.5 |
| Modified Starch (National Starch Coarse Instant Clear Jel) | 1.5 |
| Potassium sorbate | 0.1 |
| Butter flavour 2807 | 0.01 |

The paste and BMP solution comprised the following:

|  | % w/w |
|---|---|
| Buttermilk BMP Solution | 65 |
| Mycoprotein paste | 35 |

The buttermilk solution comprised the following:

|  | % w/w |
|---|---|
| Water | 96.5 |
| Buttermilk powder | 3.5 |

The buttermilk powder was added to water to reconstitute it and provide the buttermilk (BMS) solution. Mycoprotein paste was added at 35% w/w to the buttermilk solution and the combination was left for 30 minutes before being homogenised at 200 Bar using a Gaulin dairy homogeniser. Thereafter, the mixture was heated up to 55° C. and the other components of the water phase were added using an Ytron mixer which is arranged to achieve emulsification of the oil and water phases.

Preparation of Oil Phase
This comprises the following:

|  | % w/w |
|---|---|
| Oil blend (Grinstead PS209) | 38.99 |
| Dimodan OT | 0.6 |
| Pectin Grinsted PS209 | 0.4 |
| Beta carotene | 0.002 |
| Butter flavour 2822 | 0.01 |

The oil blend was heated to 50° C. and blended with the other ingredients to prepare the oil phase.

Preparation of Low Fat Spread

The oil phase was added to an emulsion tank and the water phase was added slowly thereto. The product was processed using a Krepaco Scrape Surface Heat Exchanger using three barrels. The emulsion was heated to 80° C., cooled to 50° C., thereafter cooled to 10° C. and pin worked. The low fat spread was then collected in tubs.

The spread was found to have a slightly open coarse texture; the melt down was very good; the spreadability and flavour release were good.

The spread prepared has a mycoprotein paste content of 20% w/w which delivers about 4% w/w of paste solids. The nutrient levels may be calculated based on details in Table 7b.

Table 15 details nutrient levels supplied by mycoprotein in two 10 g servings of the spread at various paste inclusions.

Preparing low fat spread in the manner described enables advantageously high levels of important nutrients to be supplied whilst not affecting significantly the eating quality.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

The invention claimed is:

1. A method of preparing a dessert, milk drink or low fat spread, the method comprising contacting an aqueous formulation with one or more other ingredients of said dessert, milk drink or low fat spread, wherein said aqueous formulation is prepared in a method which comprises:

provided a mixture which includes edible fungi in an aqueous liquid and subjecting the mixture to a size reduction process in order to produce an aqueous formulation comprising edible fungal particles arranged to act as a fat mimetic, said particles having a dimension in a first direction of at least 1 µm and less than 200 µm, wherein said dimension in said first direction is a maximum dimension of said particles, wherein said edible fungi include at least 80 weight percent (wt. %) of fungal mycelia.

2. A method according to claim 1, wherein said edible fungi is selected from fungi imperfecti.

3. A method according to claim 1, wherein said edible fungi comprise cells of a *Fusarium* species.

4. A method according to claim 1, wherein edible fungi in said mixture prior to said size reduction process have a maximum dimension in a first direction of at least 400 µm.

5. A method according to claim 1, wherein said mixture includes at least 3% w/w and less than 20% w/w of said edible fungi on a dry matter basis.

6. A method according to claim 1, wherein said aqueous liquid comprises water having dissolved and/or suspended solids.

7. A method according to claim 1, wherein said mixture is prepared by contacting said edible fungi and said aqueous liquid wherein said edible fungi are in the form of a paste which comprises at least 10% w/w edible fungi on a dry matter basis.

8. A method according to claim 1, the edible fungal particles having an average aspect ratio of less than 70.

9. A method according to claim 1, wherein the aqueous formulation comprises at least 2% w/w and less than 10% w/w of edible fungi on a dry matter basis in the dessert, milk drink, or low fat spread.

10. A method according to claim 1, comprising contacting the edible fungi with milk or milk powder.

11. A method according to claim 1, wherein a dessert is prepared and wherein the dessert is ice-cream.

12. The method of claim 1, wherein the particles are at least 5 µm in the first dimension.

13. The method of claim 1, wherein the particles are at least 10 µm in the first dimension.

14. A method according to claim 1, which is a method of preparing a dessert or a low fat spread.

15. A method according to claim 1, which is a method of preparing a dessert.

* * * * *

UNITED STATES PATENT AND TRADEMARK OFFICE
CERTIFICATE OF CORRECTION

PATENT NO. : 7,635,492 B2
APPLICATION NO. : 10/476751
DATED : December 22, 2009
INVENTOR(S) : Finnigan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 955 days.

Signed and Sealed this

Ninth Day of November, 2010

David J. Kappos
*Director of the United States Patent and Trademark Office*